US00PP37195P2

(12) United States Plant Patent
Nelson et al.

(10) Patent No.: US PP37,195 P2
(45) Date of Patent: Jan. 6, 2026

(54) STRAWBERRY PLANT NAMED 'Emerald'

(50) Latin Name: ***Fragaria* x *ananassa***
Varietal Denomination: Emerald

(71) Applicant: Fragaria Plant Sciences, B.V., Veldhoven (NL)

(72) Inventors: Jonathan R. Nelson, Watsonville, CA (US); Daniel S. Nelson, Watsonville, CA (US); Scott C. Nelson, Cardiff, CA (US); Jeffrey D. Nelson, Watsonville, CA (US)

(73) Assignee: Fragaria Plant Sciences, B.V., Veldhoven (NL)

( * ) Notice: Subject to any disclaimer, the term of this patent is extended or adjusted under 35 U.S.C. 154(b) by 0 days.

(21) Appl. No.: 18/988,701

(22) Filed: Dec. 19, 2024

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208
CPC ..... A01H 5/08; A01H 5/00; A01H 6/7409; A01H 6/74
See application file for complete search history.

(56) References Cited

U.S. PATENT DOCUMENTS

| | | | | |
|---|---|---|---|---|
| PP29,794 P2 | 11/2018 | Nelson et al. | | |
| PP30,213 P2 * | 2/2019 | Weber | A01H 6/7409 | Plt./208 |
| PP35,047 P2 * | 3/2023 | Nelson | | Plt./208 |
| PP36,113 P2 * | 9/2024 | Nelson | | Plt./208 |

* cited by examiner

*Primary Examiner* — June Hwu
(74) *Attorney, Agent, or Firm* — Foley & Lardner LLP

(57) ABSTRACT

This invention relates to a new and distinct variety of strawberry plant named 'EMERALD'. This new strawberry plant named 'EMERALD' is primarily adapted to the growing conditions of the central coast of California, and is primarily characterized by its light red fruit color, medium fruit size and conical fruit shape; excellent fruit flavor, excellent skin quality, with seeds held even with the surface; fruiting trusses very consistent from plant to plant, containing four to five fruits on every truss; strong June-bearer plant, with one large flush of flowers; medium plant size, semi-upright plant habit, with sparse to medium density and strong vigor; and large foliage size, which is strongly to slightly concave.

5 Drawing Sheets

Latin name of the genus and species of the plant claimed: *Fragaria* x *ananassa.*
Variety denomination: 'EMERALD'.

BACKGROUND OF THE INVENTION

The present invention relates to a new and distinct strawberry variety named 'EMERALD'. This new variety is a result of a controlled cross made in 2017 in an ongoing breeding program between strawberry variety designated 'Inspire' as the seed (female) parent, and strawberry variety designated 'Malling Centenary' as the pollen (male) parent. The variety is botanically known as *Fragaria* x *ananassa.*

The seedling resulting from the aforementioned cross was selected from a controlled breeding plot in Santa Cruz County, California in the spring of 2019. After its selection, the new variety was asexually propagated by stolons in San Joaquin County, California. The new variety was tested extensively over the next several years in fruiting fields in Santa Cruz County, California. This propagation has demonstrated that the combination of traits disclosed herein as characterizing the new variety are fixed and remain true-to-type through successive generations of asexual reproduction.

BRIEF SUMMARY OF THE INVENTION

'EMERALD' is primarily adapted to the climate and growing conditions of the central coast of California. The nearby Pacific Ocean provides the humidity and moderate temperatures needed to produce a strong, vigorous plant and maintain fruit quality during the April through July production months.

The following traits have been repeatedly observed and are determined to be unique characteristics of 'EMERALD', which in combination distinguish this strawberry plant as a new and distinct variety:

1. Fruit is light red in color, medium in size and conical in shape;
2. Fruiting trusses are very consistent from plant to plant, containing four to five fruits on every truss;
3. Plant is a strong June-bearer, with one large flush of flowers;
4. Plant is medium in size, semi-upright in habit, with sparse to medium density and strong vigor; and
5. Foliage is large in size, and strongly to slightly concave.

The strawberry variety that is believed to be most closely related to the new variety 'EMERALD' is 'FPS-15.2016-31' (U.S. Plant Pat. No. 36,113). In side-by-side comparisons to the similar strawberry variety 'FPS-15.2016-31', 'EMERALD' differs by the following combination of characteristics as described in Table 1.

TABLE 1

| Characteristic | 'FPS-17.6597-3' | 'FPS-15.2016-31' (U.S. Plant Pat. No. 36,113) |
|---|---|---|
| Fruit: flesh color | Light red | Red |
| Fruit: firmness of flesh | Firm (726) | Medium |
| Fruit: position of calyx | Level | Level |
| Fruit: keeping quality | Very good | Good |
| Plant: size | Large | Medium |
| Stolon: anthocyanin coloration | Greyed purple group (185A) | Red purple group (59B) |
| Stolon: anthocyanin intensity | Strong | Very strong |
| Petiole: length | Long | Medium |
| Foliage: size | Large | Medium |
| Foliage: shape in cross section | Strongly to slightly concave | Slightly concave |
| Petiole: attitude of hairs | Upward to slightly outward | Slightly outward |

For identification, a series of molecular markers have been determined for this new variety.

'EMERALD' differs from its parents, 'Inspire' and 'Malling Centenary' by the following combination of characteristics as described in Tables 2 and 3.

TABLE 2

| Characteristic | 'FPS-17.6597-3' | 'Inspire' (U.S. Plant Pat. No. 29,794) |
|---|---|---|
| Fruit: position of calyx | Level | Inserted |
| Plant: size | Large | Medium |
| Petiole: length | Long | Short |
| Foliage: shape in cross section | Strongly to slightly concave | Flat to slightly convex |
| Petiole: attitude of hairs | Upward to slightly outward | Strongly outward |

TABLE 3

| Characteristic | 'FPS-17.6597-3' | 'Malling Centenary' |
|---|---|---|
| Plant: size | Large | Medium |
| Fruit: size | Medium to large (26 g. avg.) | Small to medium (20 g. avg.) |
| Flower: timing | Mid to late | Early |
| Stipule: anthocyanin intensity | Strong | Very weak |
| Fruit quantity per truss | Medium (4 to 5) | Low (3 to 4) |

BRIEF DESCRIPTIONS OF THE PHOTOGRAPHS

The accompanying color photographs illustrate the overall appearance of typical specimens of the new strawberry variety 'EMERALD' at various stages of development, as true as it is reasonably possible with color reproductions of this type. Color in the photographs may differ slightly from the color value cited in the botanical descriptions which accurately describe the color of 'EMERALD'. The depicted plant and plant parts of the new strawberry variety 'EMERALD' are approximately three to four months old. The photographs were taken in Santa Cruz County, California.

DETAILED BOTANICAL DESCRIPTION

Figure 1:
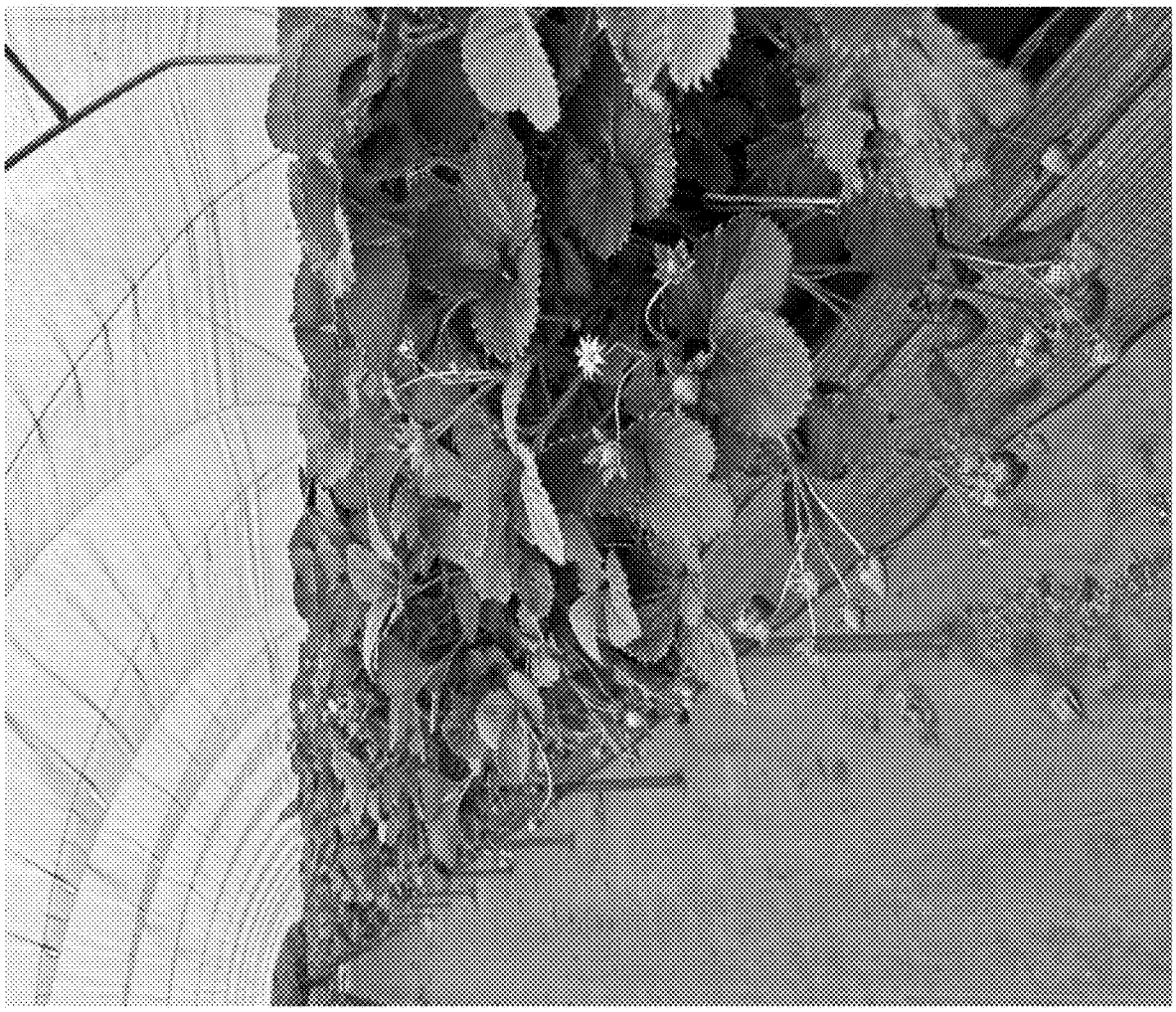
FIG. 1 shows fruiting field characteristics of 'EMERALD', taken in the month of May 2024.
Figure 2:
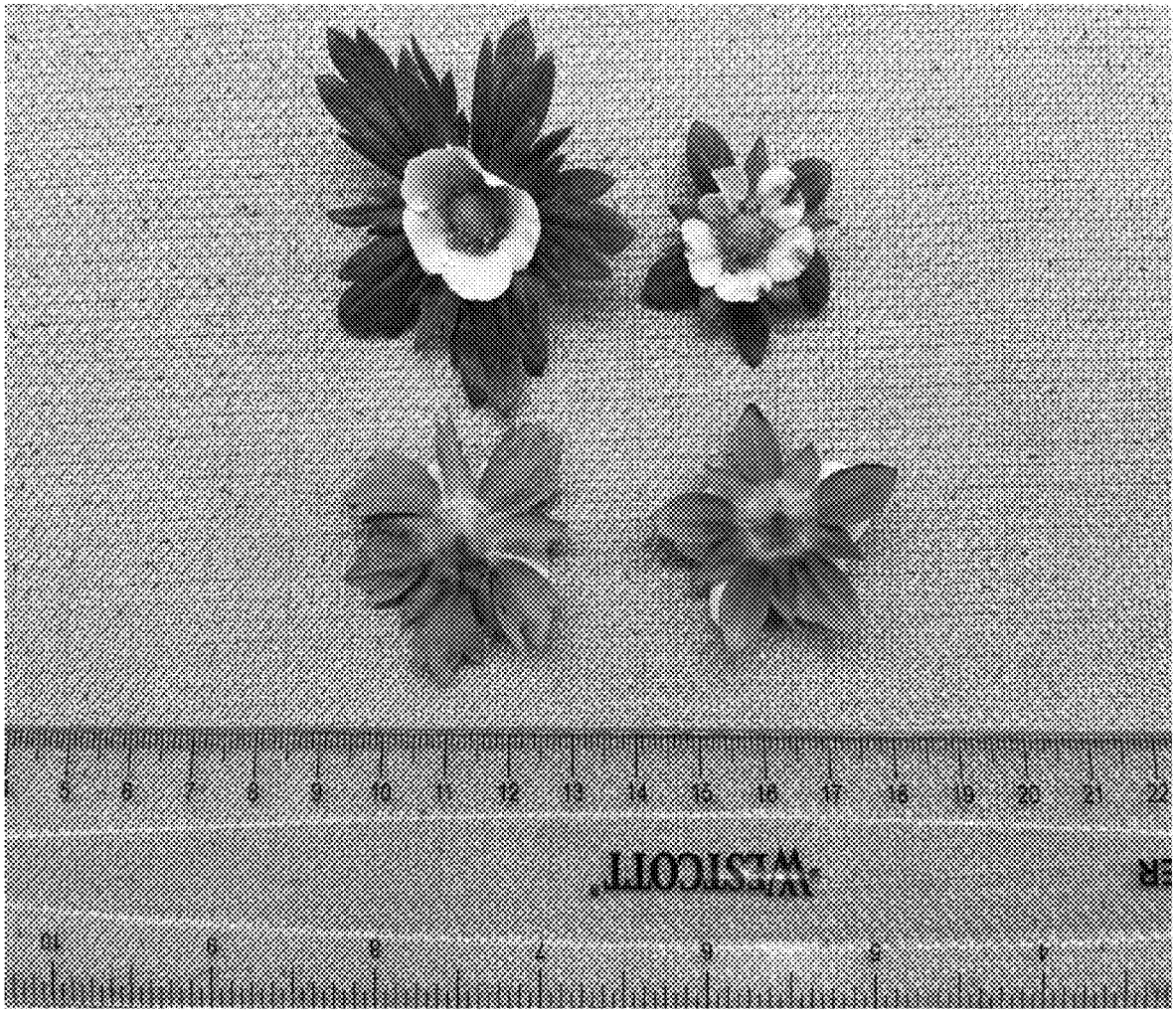
FIG. 2 shows upper and lower surfaces of flower and flower parts of 'EMERALD', taken in the month of May 2023.
Figure 3:
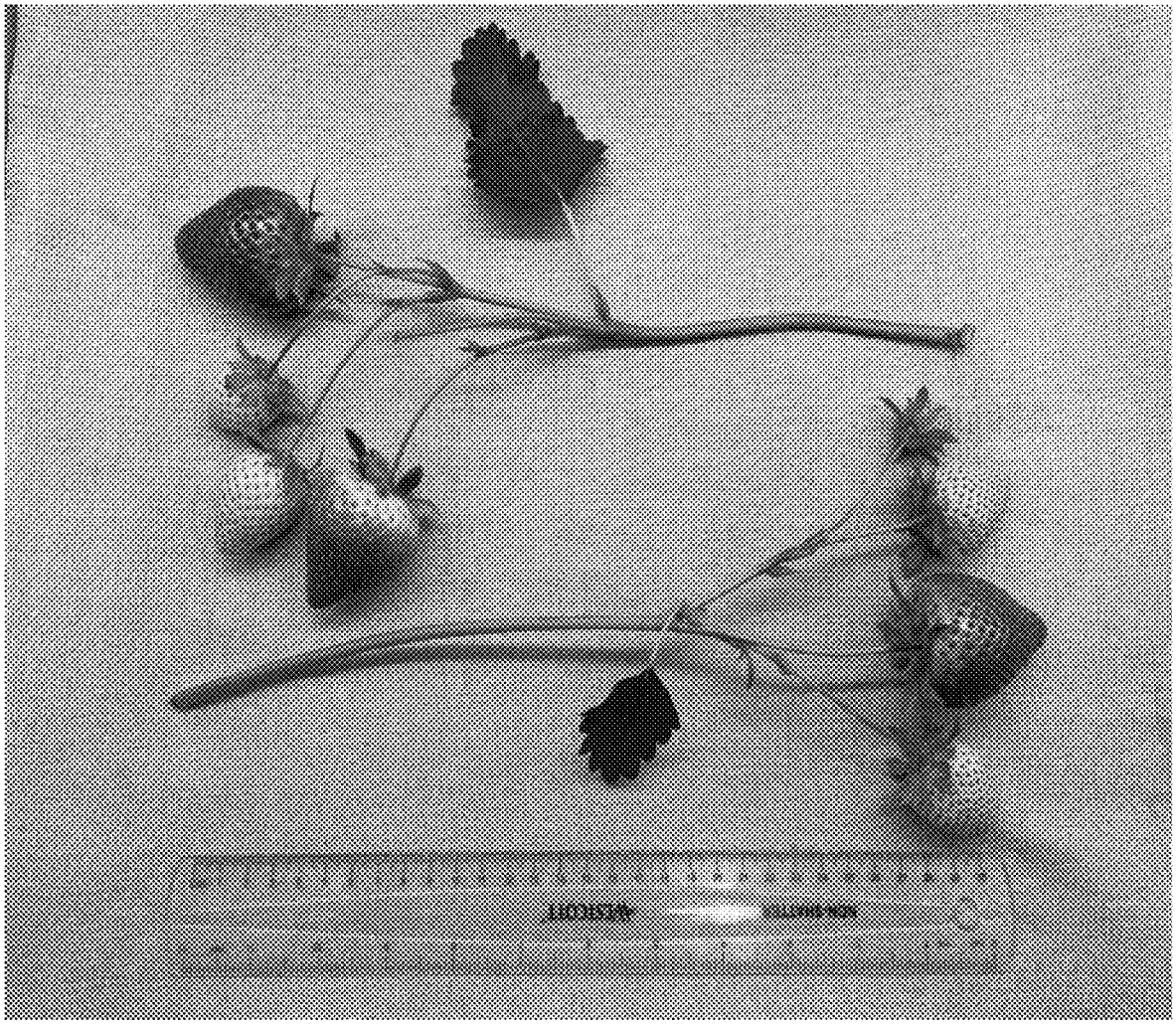
FIG. 3 shows typical fruiting truss and truss parts of 'EMERALD', taken in the month of May 2023.
Figure 4:
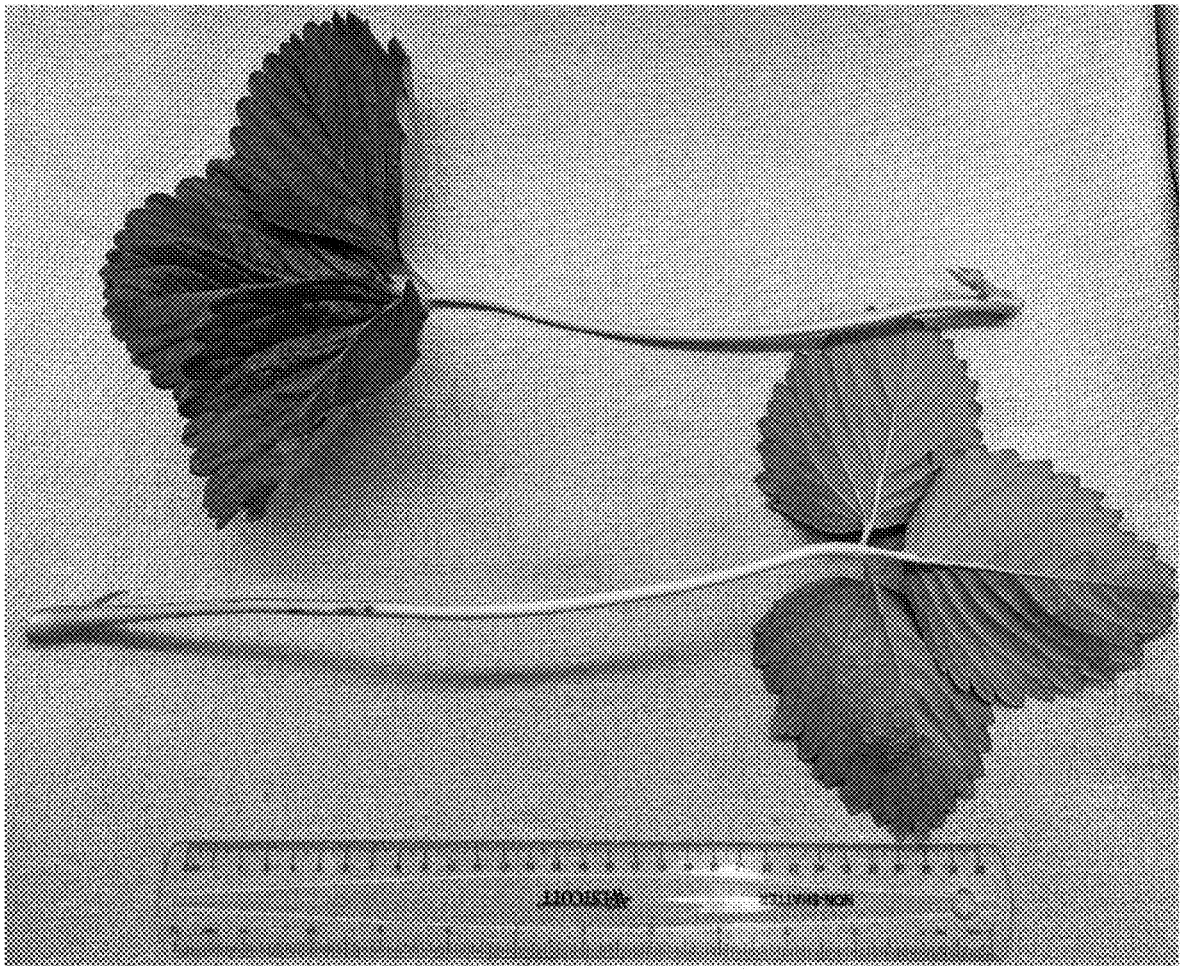
FIG. 4 shows upper and lower surfaces of leaf and leaf parts of 'EMERALD', taken in the month of May 2023.
Figure 5:
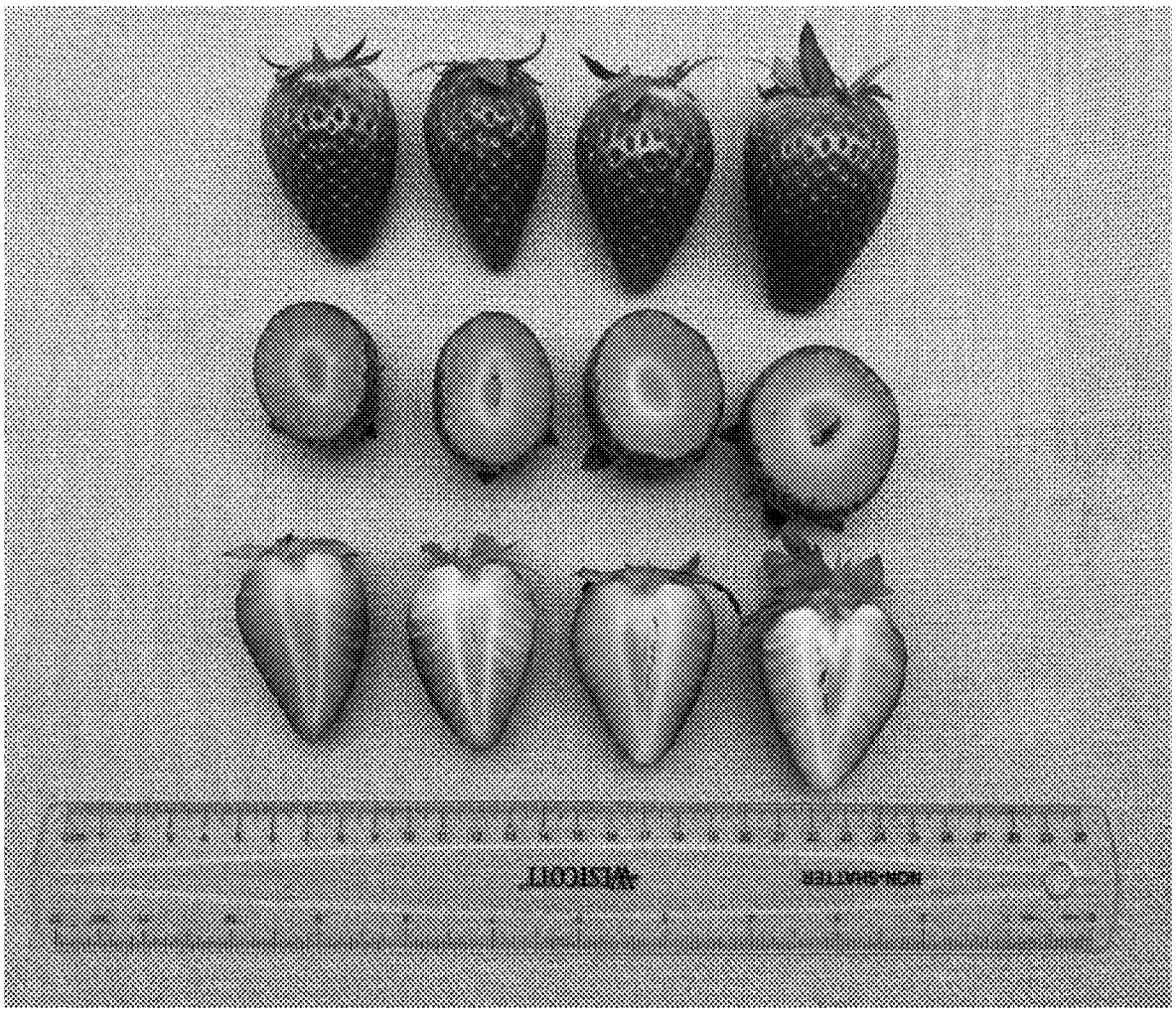
FIG. 5 shows internal and external mature fruit characteristics of 'EMERALD', taken in the month of May 2023.

The new variety 'EMERALD' has not been observed under all possible environmental conditions. The characteristics of the new variety 'EMERALD' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'EMERALD', unless otherwise noted, are based on observations taken during the 2023 growing season in Santa Cruz County, California. These measurements and ratings were taken from plants of 'EMERALD' dug from a low-elevation nursery located in San Joaquin County, California in December 2022 and planted three to four months later in Santa Cruz County, California. The approximate age of the observed plants is three to four months. Yield observations including average weight and marketable yield, along with fruit quality characteristics including soluble solids, are averaged from four years of data collected from the 2020 through 2023 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London, Sixth Edition (2015).

The following characteristics describe fruit, plant, stolon, foliage, fruiting truss, flower, reproductive organs and pest and disease characteristics of the new strawberry 'EMERALD'.

Fruit characteristics:

*Color of mature fruit.*—44A (vivid red).
*Color of internal flesh.*—44C (light red).
*Color of core.*—44C (light red).
*Average length (cm).*—4.7.
*Average width (cm).*—3.7.
*Size.*—Medium.
*Average length/width ratio.*—1.28 (ranges from slightly longer than broad to much longer than broad).
*Hollow center average length (mm).*—48.7.
*Hollow center average width (mm).*—9.0.
*Hollow center expression.*—Absent or very weak.
*Season average weight (gm).*—26.1.
*Marketable yield season (gm/plant).*—366.
*Predominant shape.*—Ranges from conical to ovoid (ovate).
*Difference in shape between primary and secondary fruit.*—None or very slight.
*Band without achenes.*—Narrow.
*Evenness of surface.*—Even or very slightly uneven.
*Evenness of color.*—Even or very slightly uneven.

*Glossiness*.—Strong.
*Insertion of achenes*.—Level with surface.
*Average calyx diameter* (*cm*).—4.5.
*Position of calyx attachment*.—Level.
*Attitude of sepals*.—Outward.
*Size of calyx in relation to fruit diameter*.—Slightly larger.
*Adherence of calyx* (*when fully ripe*).—Strong.
*Firmness of flesh*.—Firm.
*Fruit market*.—Fresh.
*Shape of apex*.—Acute.
*Post-harvest fruit longevity* (*at* 1 *to* 3 *degrees Celsius*) .—Excellent (10 to 14 days).
*Distribution of red color of the flesh*.—Marginal and central.
*Flavor*.—Excellent (high sugar/acid ratio, high sweetness and great aroma).
*Soluble solids* (*% brix-titratable acidity*).—9.2.
*Achene color, shaded side*.—153A (yellow green group).
*Achene color, sun-exposed side*.—183C (greyed purple group).
*Achene average length* (*mm*).—1.6.
*Achene average width* (*mm*).—1.3.
*Achene average weight* (*mg*).—0.63.
*Achene average quantity per berry*.—256.
*Achene shape*.—Ovate.

Time of flowering:
*Flowering season* (50% *of plants with at least one flower*).—Medium (April in Watsonville, California).
*Maturing season* (50% *of plants with mature fruit*.—Medium (May in Watsonville, California).
*Flowering season*.—April to June (in Watsonville, California).
*Harvest season*.—May to July (in Watsonville, California).
*Harvest maturity*.—Mid-season (May to June).
*Plant hardiness*.—Zone 9 (USDA Plant Hardiness Zone Map).
*Type of bearing*.—Not remontant.

Plant characteristics:
*Average height* (*cm*).—37.4.
*Average spread* (*cm*).—42.8.
*Average crowns per plant*.—2.8.
*Size*.—Ranges from medium to large.
*Habit*.—Semi-upright.
*Density*.—Ranges from sparse to medium.
*Vigor*.—Strong.

Stolon characteristics:
*Color*.—145A (yellow green group).
*Anthocyanin coloration*.—185A (greyed purple group).
*Anthocyanin intensity*.—Strong.
*Pubescence*.—Dense.
*Attitude of hairs*.—Upward.
*Average quantity in nursery* (*per square foot*).—5 to 6 (medium).
*Average diameter at first bract* (*mm*).—4.4 (thick).
*Length from mother plant to first daughter* (*cm*).—31.2.

Terminal leaflet characteristics:
*Average length* (*cm*).—11.4.
*Average width* (*cm*).—10.3.
*Average area terminal* ($cm^2$).—116.6.
*Average length/width ratio*.—1.11 (longer than broad).
*Shape of base*.—Acute.
*Shape of apex*.—Obtuse.
*Margins* (*shape of teeth*).—Obtuse (serrate to crenate).
*Average serrations per leaf*.—22.8.

Foliage characteristics:
*Color of upper surface*.—137B (medium green).
*Color of lower surface*.—N148C (yellow green group).
*Color of venation, upper surface*.—151D (yellow green group).
*Color of venation, lower surface*.—145C (yellow green group).
*Number of leaflets*.—3.
*Leaf size*.—Large.
*Average length* (*cm*).—16.3.
*Average width* (*cm*).—22.1.
*Average area foliage* ($cm^2$).—241.7.
*Shape in cross section*.—Strongly to slightly concave.
*Interveinal blistering*.—Medium.
*Texture of upper surface*.—Smooth.
*Texture of lower surface*.—Medium density of pubescence.
*Venation pattern*.—Pinnate reticulate.
*Leaf glossiness*.—Ranges from medium to strong.
*Leaf variegation*.—Absent.

Petiole characteristics:
*Petiole color*.—145B (yellow green group).
*Petiole average length* (*cm*).—25.8.
*Petiole average diameter* (*mm*).—5.4.
*Attitude of hairs*.—Ranges from upward to slightly outward.
*Frequency of bract leaflets*.—0% (none).
*Size of bract leaflets*.—N/A.
*Pubescence*.—Moderate.
*Petiolule color*.—145B (yellow green group).
*Petiolule average length* (*mm*).—11.3.
*Petiolule average diameter* (*mm*).—2.7.

Stipule characteristics:
*Color*.—146D (yellow green group).
*Anthocyanin coloration*.—60C (red purple group).
*Anthocyanin intensity*.—Strong.
*Average length* (*mm*).—30.5.
*Average width* (*mm*).—8.8.
*Shape*.—Triangular.
*Texture*.—Medium.
*Shape of base*.—N/A.
*Shape of apex*.—Acute.
*Margins*.—Entire (smooth).

Fruiting truss characteristics:
*Anthocyanin coloration*.—183D (greyed purple group).
*Anthocyanin intensity*.—Absent or very weak.
*Average length at maturity* (*cm*).—30.8.
*Position relative to foliage*.—Ranges from level with to above.
*Flower quantity* (*season average per plant*).—30 to 35 (medium).
*Average fruit quantity per truss*.—4.4 (medium).
*Attitude at first pick*.—Prostrate.
*Primary pedicel color*.—144B (yellow green group).
*Primary pedicel average length* (*cm*).—7.6.
*Primary pedicel average diameter* (*mm*).—2.4.
*Pedicel attitude of hairs*.—Ranges from upward to slightly outward.
*Pedicel texture*.—Weak.
*Primary peduncle color*.—144B (yellow green group).
*Primary peduncle average length* (*cm*).—16.3.
*Primary peduncle average diameter* (*mm*).—4.4.
*Peduncle texture*.—Weak.

Flower characteristics:

*Petal color, upper surface.*—155C (white group).
*Petal color, lower surface.*—155C (white group).
*Petal average length (mm).*—12.0.
*Petal average width (mm).*—12.6.
*Petal average length/width ratio.*—0.95 (as long as broad).
*Average petal quantity per flower.*—5.0.
*Petal shape.*—Rounded.
*Petal texture (upper surface).*—Smooth.
*Petal texture (lower surface).*—Smooth.
*Petal shape of base.*—Acute.
*Petal shape of apex.*—Rounded.
*Petal margins.*—Entire (smooth).
*Sepal color, upper surface.*—143A (green group).
*Sepal color, lower surface.*—143C (green group).
*Sepal average length (mm).*—17.3.
*Sepal average width (mm).*—9.2.
*Sepal average length/width ratio.*—1.89.
*Average sepal quantity per flower.*—10.
*Sepal shape.*—Elliptical.
*Sepal texture (upper surface).*—Light.
*Sepal texture (lower surface).*—Smooth.
*Sepal shape of apex.*—Acute.
*Sepal margins.*—Serrated margins.
*Flower bud color.*—144C (yellow green group).
*Flower bud shape.*—Bell.
*Flower bud average length (mm).*—9.3.
*Flower bud average diameter (mm).*—8.8.
*Corolla average diameter (mm).*—26.2 (medium).
*Flower average depth (mm).*—5.1 (shallow).
*Calyx average diameter (mm).*—44.0.
*Size of calyx relative to corolla.*—Larger.
*Arrangement of petals.*—Overlapping.
*Size of inner calyx relative to outer calyx.*—Smaller.

Reproductive organs:

*Anther color.*—13A (yellow group).
*Filament color.*—145C (yellow green group).
*Filament average length (mm).*—2.2.
*Anther average length (mm).*—1.9.
*Anther average width (mm).*—1.0.
*Anther shape.*—Broad elliptic.
*Pollen amount.*—Abundant.
*Ovary color.*—147C (yellow green group).
*Style color.*—151C (yellow green group).
*Pistil average quantity per flower.*—320.
*Pistil average length (mm).*—1.0.
*Style average length (mm).*—1.0.
*Stigma average diameter (mm).*—0.2.
*Stigma shape.*—Rounded.

Disease and pest reactions:

*Powdery mildew (Sphaerotheca macularis).*—Ranges from moderately resistant to moderate.
*Angular leaf spot (Xanthomonas fragariae).*—Moderate.
*Botrytis fruit rot (Botrytis cinerea).*—Moderately susceptible.
*Fusarium wilt (Fusarium oxysporum).*—Resistant.
*Anthracnose crown rot (Colletotrichum fragariae).*—Unknown.
*Two-spotted spider mite (Tetranychus urticae).*—Moderately susceptible.

We claim:

1. A new and distinct strawberry plant named 'EMERALD', as herein described in the specification.

* * * * *